United States Patent [19]

Hangartner

[11] Patent Number: 5,673,303
[45] Date of Patent: Sep. 30, 1997

[54] METHOD AND APPARATUS FOR THE EVALUATION OF STRUCTURAL WIDTH AND DENSITY BY COMPUTED TOMOGRAPHY

[75] Inventor: Thomas Niklaus Hangartner, Xenia, Ohio

[73] Assignee: Wright State University, Dayton, Ohio

[21] Appl. No.: 752,023

[22] Filed: Nov. 19, 1996

Related U.S. Application Data

[63] Continuation-in-part of Ser. No. 424,841, Apr. 19, 1995, Pat. No. 5,594,775.

[51] Int. Cl.$^6$ .................................................. G01D 18/00
[52] U.S. Cl. .................................................. 378/207; 378/54
[58] Field of Search ........................ 378/207, 51, 54, 378/50

[56] References Cited

U.S. PATENT DOCUMENTS 4,721,112  1/1988  Hirano et al. .................................. 378/54

OTHER PUBLICATIONS

"Evaluation of Cortical Bone by Computed Tomography", Thomas N. Hangartner and Vicente Gilsanz, Journal of Bone and Mineral Research, vol. II, pp. 1518–1525, No. 10, 1996.
"Constant Cortical Density is a Requirement for the Accurate Measurement of Cortical Thickness by CT" Hangartner et al, Bone and Mineral, Supplement 2 to Vol. 25, Apr. 1994, p. S4.
"Measurement of Cortical Bone by Computed Tomography" Hangartner et al., 9th International Bone Densitometry Workshop Abstracts, Sep. 26–30, 1992, p. 30.

"Thickness of the Cortical Layer as an Estimae of Mineral Content of Human Finger Bones", by P. Virtama, M.D. et al., Vo. XXXIII, No. 385, Rentgen Dept. Second Medical Clinic, University Central Hospital, Helsinki, Aug. 1959.

"The Radiological Diagnosis of Osteoporosis: A New Approach", by Ellis Barnett, D.M.R.D., FFR. et al., Department of Radiology and the University Department of Medicine, Gardiner Institue, Western Infirmary, Glasgow, Apr. 1959.

"Size of Cortical Bone and Relationship to Bone Mineral Density Assessed by Quantitative Computed Tomography Image Segmentation", Olivia Louis, M.D., Ph.D. et al., Investigative Radiology, vol. 28, No. 9, 802–805, 1993.

*Primary Examiner*—Don Wong
*Attorney, Agent, or Firm*—Killworth, Gottman, Hagan & Schaeff, L.L.P.

[57] ABSTRACT

A method and apparatus are provided for the measurement of structural width and density with a CT scanner. The density of a particular structure is determined by establishing a radial density profile of a structure, identifying a peak density value along said density profile, interpolating a first curve of density versus width from a point defined by the structural width and the peak density value, and identifying a maximum density value of said first curve to establish a structural density value. The width of the structure is determined by identifying first and second radial positions corresponding to respective points on said radial density profile where the profile rises above and falls below first and second threshold values, measuring a difference between said first radial position and said second radial position, and determining the width of the structure as a function of the measured difference.

16 Claims, 5 Drawing Sheets

METHOD AND APPARATUS FOR THE EVALUATION OF STRUCTURAL WIDTH AND DENSITY BY COMPUTED TOMOGRAPHY

CROSS REFERENCE TO RELATED APPLICATIONS

This application is a Continuation-in-Part of U.S. patent application Ser. No. 08/424,841, filed Apr. 19, 1995, now U.S. Pat. No. 5,594,775.

BACKGROUND OF THE INVENTION

The present invention relates to computed tomography (CT) and in particular to the measurement of structural width with a CT scanner and to the measurement of structural density with a CT scanner where the width dimension of the structure is below the scanner's minimum resolution value.

A CT scanner is capable of indicating measurements of structural width and density. However, scanner resolution suffers significantly when the width of a structure under analysis falls below a certain limit, the scanner's minimum resolution value. Specifically, this insufficient resolution results in a misrepresentation of the true density of the structure and makes it difficult to determine the true width of the structure.

Thus, according to conventional scanning methodology, it is not possible to obtain accurate width and density measurements of structures having widths below a certain value, the scanner's minimum resolution value. Accordingly, there is a need for an improved method and apparatus for evaluating width and density of structures having widths below the minimum resolution value of the CT scanner in use.

BRIEF SUMMARY OF THE INVENTION

This need is met by the present invention wherein a method and apparatus are provided for the measurement of structural width and density with a CT scanner. Specifically, where the width dimension of the structure is below the scanner's minimum resolution value, the density of a particular structure is determined by establishing a radial density profile of a structure, identifying a peak density value along the density profile, interpolating a first curve of density versus width from a point defined by the structural width and the peak density value, and identifying a maximum density value of the first curve to establish a structural density value. The width of the structure is determined by identifying first and second radial positions corresponding to respective points on the radial density profile where the profile rises above and falls below first and second threshold values, measuring a difference between the first radial position and the second radial position, and determining the width of the structure as a function of the measured difference.

In accordance with one embodiment of the present invention, a method of measuring a structure is provided comprising the steps of: obtaining X-ray image data of a structure with a computed tomography scanner; establishing a radial density profile of the structure based upon the obtained X-ray image data; identifying a peak density value $D_1$ along the density profile; identifying a structural width $w_1$ of the structure; interpolating a first curve of density versus width from a point defined by coordinates $w_1$ and $D_1$; and identifying a maximum density value of the first curve to establish a structural density value $D_2$.

The step of interpolating the first curve preferably comprises the steps of obtaining X-ray image data of a plurality of phantoms with the computed tomography scanner wherein each of the phantoms has a known density and a plurality of known widths, plotting a series of curves, each of the curves representing peak density values of each phantom as a function of structural width, and each of the curves including a maximum peak density value, and interpolating the first curve based upon the paths of the series of curves.

The structure may be selected from the group consisting of cortical bone or trabecular bone and the first estimated structural width may correspond to the width of a cortex of a bone or of an individual trabecula.

In accordance with another embodiment of the present invention, an apparatus for measuring a structure is provided comprising: a computed tomography scanner and a digital controller in communication with the computed tomography scanner, the digital controller being programmed to establish a radial density profile of the structure based upon X-ray image data obtained by the computed tomography scanner, identify a peak density value $D_1$ along the density profile, identify a structural width $w_1$ of the structure, interpolate a first curve of density versus width from a point defined by coordinates $w_1$ and $D_1$, and identifying a maximum density value of the first curve to establish a structural density value $D_2$.

The apparatus may further comprise a display device in communication with the digital controller wherein the digital controller is further programmed to cause display of one or several of the radial density profiles, the peak density value $D_1$, the structural width $w_1$, the first curve of density versus width, and the structural density value $D_2$.

The digital controller is preferably programmed to cause phantom X-ray image data of a plurality of phantoms to be stored and plotted as a series of curves, the phantom X-ray image data being indicative of a peak density value of each phantom as a function of phantom structural width, each of the phantoms having a known density and a plurality of known widths, and to interpolate the first curve based upon the paths of the series of curves.

In accordance with yet another embodiment of the present invention, a method of measuring a structure is provided comprising the steps of: obtaining X-ray image data of a structure with a computed tomography scanner; establishing a radial density profile of the structure from the obtained X-ray image data; calculating a first threshold value and a second threshold value; identifying a first radial position corresponding to a point on the radial density profile where the radial density profile rises above the first threshold value; identifying a second radial position corresponding to a point on the radial profile where the radial density profile falls below the second threshold value; measuring a difference between the first radial position and the second radial position; and determining the width of the structure as a function of the measured difference.

The first threshold value is preferably calculated by multiplying a first density difference by an optimized percentage threshold, and the second threshold value is calculated by multiplying a second density difference by the optimized percentage threshold. The first density difference is preferably a difference between a density of the structure and a density of a first adjacent material, and the second density difference is preferably a difference between the density of the structure and a density of a second adjacent material. The first density value is preferably the sum of the

3 first threshold value and the density of the first adjacent material, and the second density value is the sum of the second threshold value and the density of the second adjacent material.

Accordingly, it is an object of the present invention to provide a method and apparatus for determining the width and/or density of a structure having a width dimension smaller than the width dimension corresponding to the minimum resolution value of the particular CT scanner in use.

DETAILED DESCRIPTION OF THE INVENTION

As noted above, the present invention provides accurate measurement of structural width and accurate measurement of structural density even where a structure of interest has a width below the minimum resolution value of a particular CT scanner being used.

To practice the structural density measurement of the present invention, the width of a number of phantoms are given as predetermined or known values and the width of the structure of interest is either estimated from X-ray image data or also given as a predetermined or known value. Further, referring to FIGS. 1–3 and 5, a series of calibration curves 30 unique to the particular scanner in use are derived from radial density profiles of a plurality of phantoms. A radial density profile is established by obtaining X-ray image data of the structure with a computed tomography scanner and plotting measured density versus radial position in the manner described below with reference to FIG. 2. Radial position, as utilized in the present specification and claims, includes locations along a radius of a circular structure and, more generally, includes locations along any substantially linear path across a structure, preferably where the linear path substantially follows a direction of maximum change of structural density values.

Figure 1:
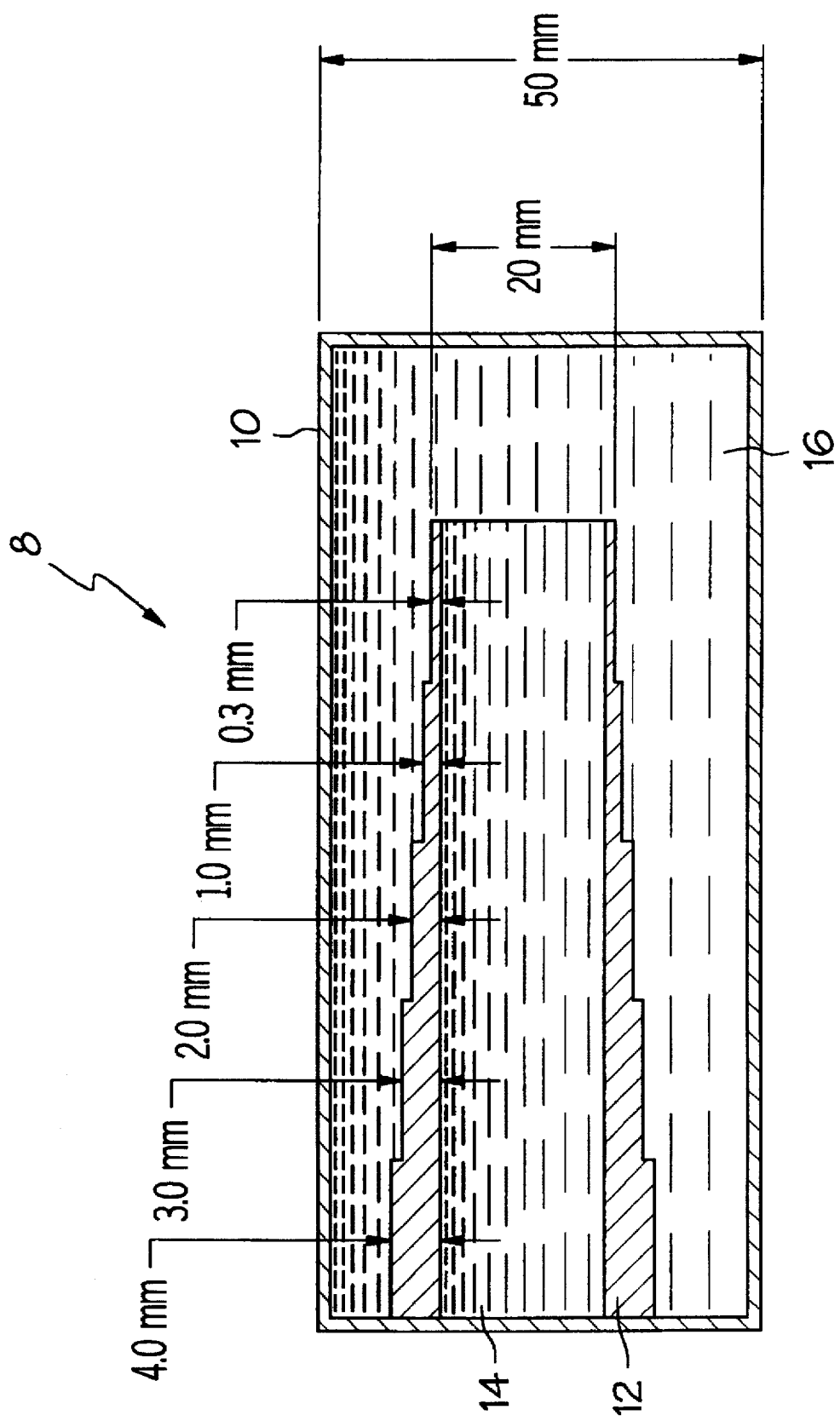
FIG. 1 is a cross-sectional view of a phantom according to the present invention.
Figure 2:
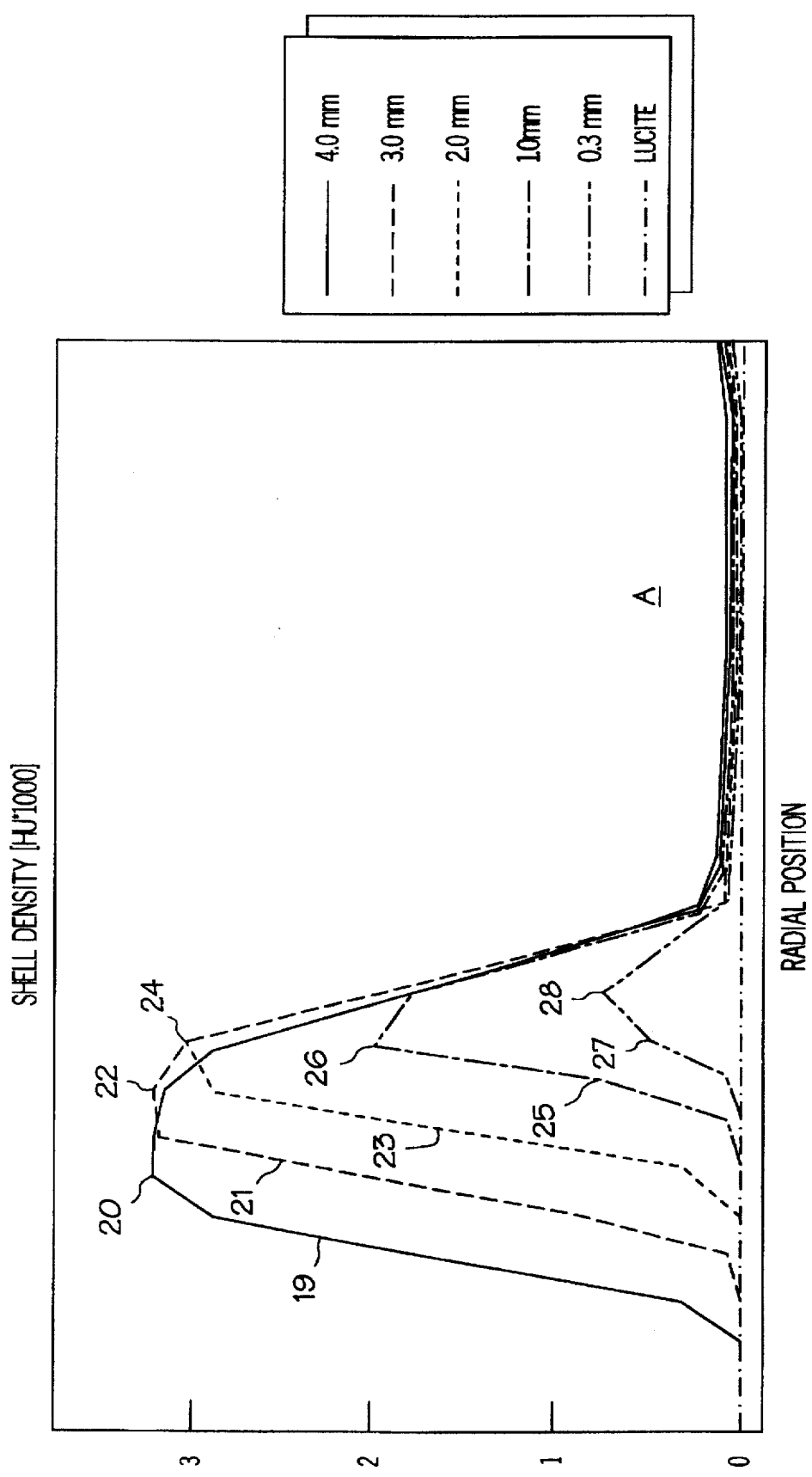
FIG. 2 is a graphical illustration of a plurality of radial density profiles according to the present invention.

A suitable phantom 8 comprises an outer cylinder of LUCITE® 10 with an inner stepped cylindrical insert 12 of aluminum, PVC, or some other test material. The inner stepped cylindrical insert 12 has a predetermined or known density and includes cortical portions having five discrete cortical widths: 0.3 mm, 1.0 mm, 2.0 mm, 3.0 mm, 4.0 mm. The radial density profiles corresponding to each discrete thickness wall portion of the phantom 8 are illustrated in FIG. 2 where a 4.0 mm radial density profile 19 corresponds to a scan obtained at the 4.0 mm cortical portion of the phantom 8 and has a 4.0 mm peak density value 20; a 3.0 mm radial density profile 21 corresponds to a scan obtained at the 3.0 mm cortical portion of the phantom 8 and has a 3.0 mm peak density value 22; a 2.0 mm radial density profile

4

23 corresponds to a scan obtained at the 2.0 mm cortical portion of the phantom 8 and has a 2.0 mm peak density value 24; a 1.0 mm radial density profile 25 corresponds to a scan obtained at the 1.0 mm cortical portion of the phantom 8 and has a 1.0 mm peak density value 26; and, a 0.3 mm radial density profile 27 corresponds to a scan obtained at the 0.3 mm cortical portion of the phantom 8 and has a 0.3 mm peak density value 28.

Figure 5:
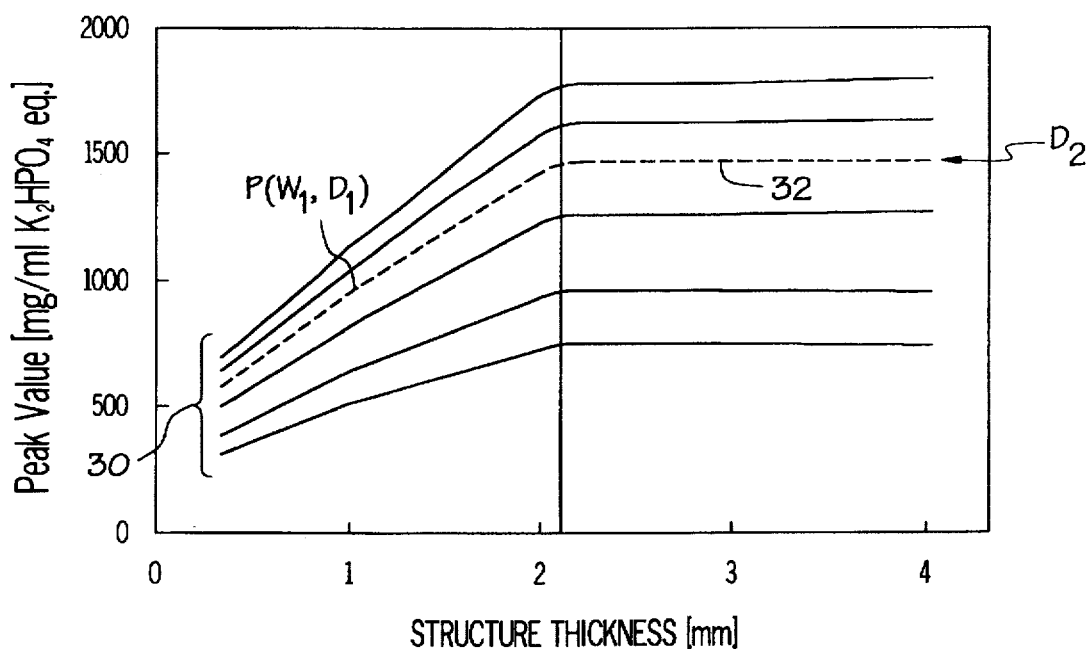
FIG. 5 is a graphical illustration of a series of calibration curves and a method of measuring structural density according to the present invention.

A single calibration curve 30' comprises a plot of the peak density values 20, 22, 24, 26, and 28 of each radial density profile 19, 21, 23, 25, 27 as a function of structural thickness or width, i.e., as a function of the thickness or width of each discrete wall portion of the phantom 8. The calibration curve 30' has a resulting maximum peak density value corresponding to the portion of the curve indicated at B. The maximum peak density value indicated at B substantially corresponds to the actual density of the phantom. The series of calibration curves 30, see FIG. 5, are derived in the same manner by obtaining radial density profiles of a plurality of additional phantoms over a predetermined range of structural densities.

After the series of calibration curves 30 has been plotted, X-ray image data of a structure of interest, having a width estimated based upon the X-ray image data or a predetermined width, is obtained using a computed tomography scanner. A radial density profile of the structure similar to the profiles illustrated in FIG. 2 is established based upon the obtained X-ray image data. The peak density value $D_1$ along the density profile of the structure of interest and the structural width $w_1$ of the structure of interest are identified. Specifically, the peak density value $D_1$ may be identified automatically through the CT operating software in use or may be manually identified by observing a display of the X-ray image data. The structural width $w_1$ may be identified by referencing a previously determined value or by estimating the structural width $w_1$ from the X-ray image data. A point P defined by coordinates $w_1$ and $D_1$ is identified and a first curve 32 of density versus width including the point P is interpolated based upon the series of calibration curves 30, see FIG. 5. Finally, a maximum density value of the first curve 32 is identified to establish a structural density value $D_2$.

Figure 4:
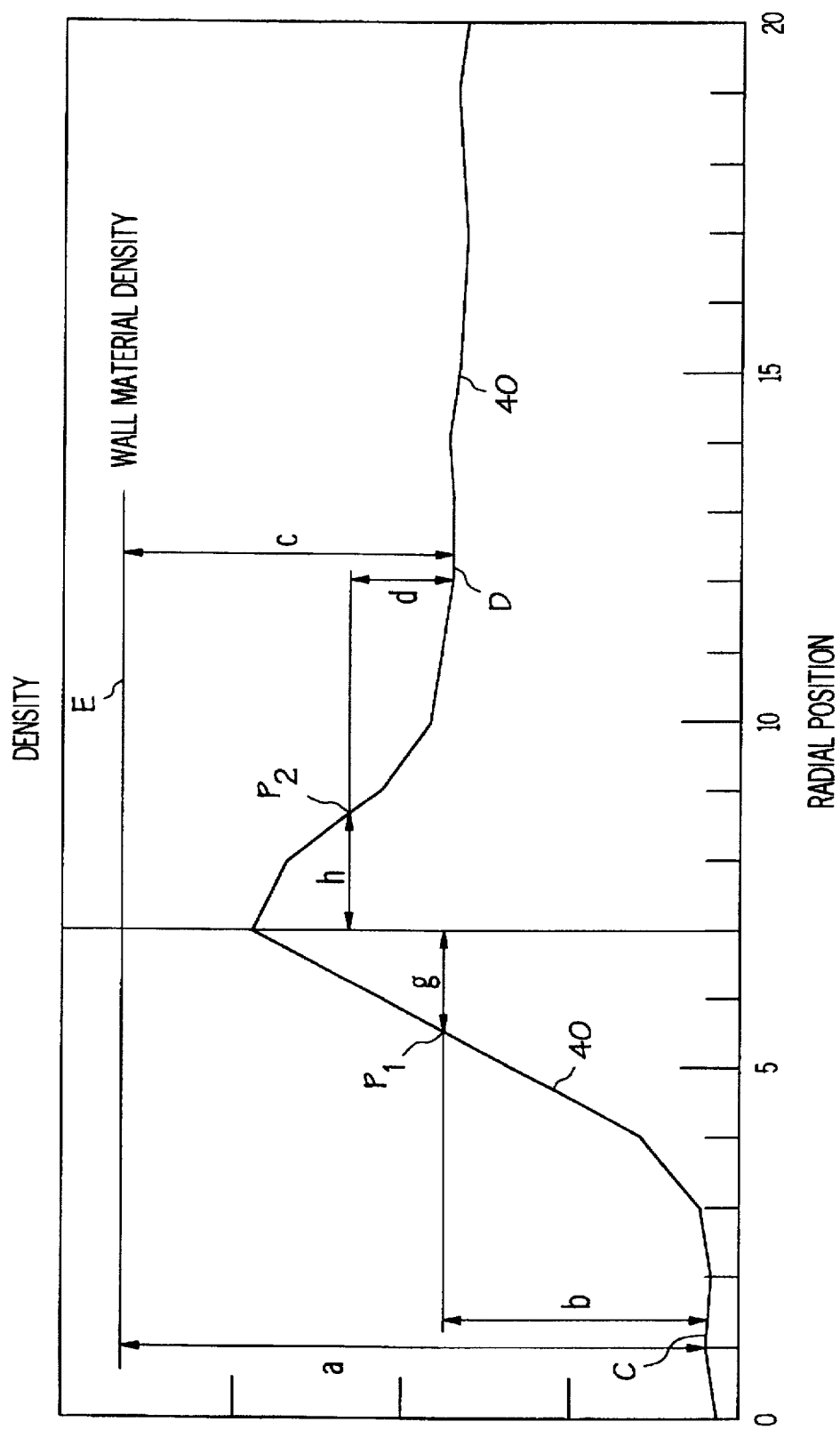
FIG. 4 is a graphical illustration of a radial density profile and a method of measuring structural width according to the present invention.

Referring now to FIG. 4, a method for measuring the width of a structure having a known density is illustrated, wherein structural width is evaluated based on an optimized fixed threshold. FIG. 4 shows a density profile of a cortical bone. The cortical bone is characterized by a known density value indicated by the line E. The density of the different materials located adjacent to the outer and inner boundary of the structure are indicated by the first series of substantially constant density values outside the structure at C and inside the structure at D. The width of the structure, in this case the cortex of a bone, is obtained by combining two half-widths, g and h. The half-width g corresponds to the half-width of the profile at a density value determined by adding a threshold b to the density value corresponding to the density at C. The half-width h corresponds to the half-width of the profile at a density value determined by adding a threshold d to the density value corresponding to the density at D.

The threshold b is calculated by multiplying an optimum percentage threshold t by the difference between the structural density, indicated at E, and the density of the material adjacent to the outer boundary of the structure (b=t×a). The threshold d is calculated by multiplying the optimum percentage threshold t by the difference between the structural density and the density of the material adjacent to the inner boundary of the structure (d=t×c). The half width g is measured at a point on the profile having a density value equal to the threshold value b added to a density value of a substantially constant portion of the density profile outside of the structure, indicated at C. The half width h is measured at a point on the profile having a density value equal to the threshold value d added to a density value of a substantially constant portion of the density profile inside of the structure, indicated at D. The two half widths, g and h, are combined to determine structural width (w=g+h).

The optimum percentage threshold t is determined by identifying, for the particular CT scanner in use, a percentage threshold t which provides the smallest overall error in width measurements for a number of phantoms having known wall widths. The optimum percentage threshold method is preferably only utilized when the density profile of the structure of interest includes a maximum density value greater than the thresholds corresponding to the half-widths g and h. Table 1 demonstrates examples of optimal thresholds found using phantoms having known wall widths for two different CT scanners:

TABLE 1

| Phantom | GE-9800 | OSTEOQUANT ® |
|---|---|---|
| Aluminum | 52% | 30% |
| PVC | 51% | 45% |

The percentage threshold appeared to be dependent on the composition of the phantom structure for the OSTEO-QUANT®. Accordingly, when employing an optimized fixed threshold to evaluate structural width, the composition of the phantom should be selected so as to correspond as closely as possible to the composition of the structure of interest. Where the structure of interest is bone, the composition of the phantom used to determine the optimum percentage threshold is preferably polyvinylchloride (PVC).

It is contemplated by the present invention that a variety of computer source codes may be utilized to perform the above described structural width measurement. An example of source code for performing the structural width measurement is presented below where, with reference to FIG. 4, "Dens" represents the measured radial density profile 40 and "N" represents the series of measured values which form the radial density profile 40. "Loc_out" represents the radial position corresponding to the point $P_1$ at which the density profile 40 crosses, i.e., rises above, an exterior threshold value "Thresh_out." "Loc_in" represents the radial position corresponding to the point $P_2$ at which the density profile 40 crosses, i.e., falls below, an interior threshold value "Thresh_in." "Loc" represents the radial location of a maximum density "Hi_dens" of the density profile 40. "Thresh_rel" is a given value representing the optimum percentage threshold t. "St_dens" is a given value representing the density of material outside the structure of interest, "M_dens" is a given value representing the density of material inside the structure of interest, and "Peak_est" is a given value representing the density of the structure of interest.

To determine structural width according to the steps set forth in the source code reproduced below, the maximum density "Hi_Dens" along the density profile 40 is located. Next, the radial position "Loc_out" corresponding to the point $P_1$ at which the density profile 40 crosses an exterior threshold value "Thresh_out" is identified and, similarly, the radial position "Loc_in" corresponding to the point $P_2$ at which the density profile 40 crosses an interior threshold value "Thresh_in" is identified. The difference between the radial positions "Loc_out" and "Loc_in" is computed to yield the structural width. As will be appreciated by one skilled in the art, the difference between the radial positions "Loc_out" and "Loc_in" is preferably converted to a metric measurement by multiplying the difference by the scanner's pixel size. For example, if the difference between the radial positions is 10 pixels and each pixel is 0.2 mm, the metric measurement of structural thickness will be 2.0 mm.

The density and width measurement processes described herein provide accurate structural measurements even if the structural width falls below the minimum resolution value of the CT scanner. Returning now to FIGS. 1 and 2, a process for determining the minimum resolution value of a particular CT scanner will be illustrated. The minimum resolution value of a CT scanner can be assessed by imaging the phantom 8 or any phantom having known widths. As noted above, the phantom 8 comprises an outer cylinder of LUCITE® 10 with an inner stepped cylindrical insert 12 of aluminum, PVC, or some other test material. The inner stepped cylindrical insert 12 includes cortical portions having five discrete cortical widths: 0.3 mm, 1.0 mm, 2.0 mm, 3.0 mm, 4.0 mm. The insert 12 is filled with a solution 14 of 150 mg/ml $K_2HPO_4$ to mimic trabecular bone. Alternatively, measurements may be performed with water or air in the center of the insert 12. The space 16 between the insert 12 and the LUCITE® container 10 is filled with water to mimic soft tissue. The phantom 8 can be scanned by itself or can be scanned after having been inserted into a whole body water phantom (not shown).

Figure 3:
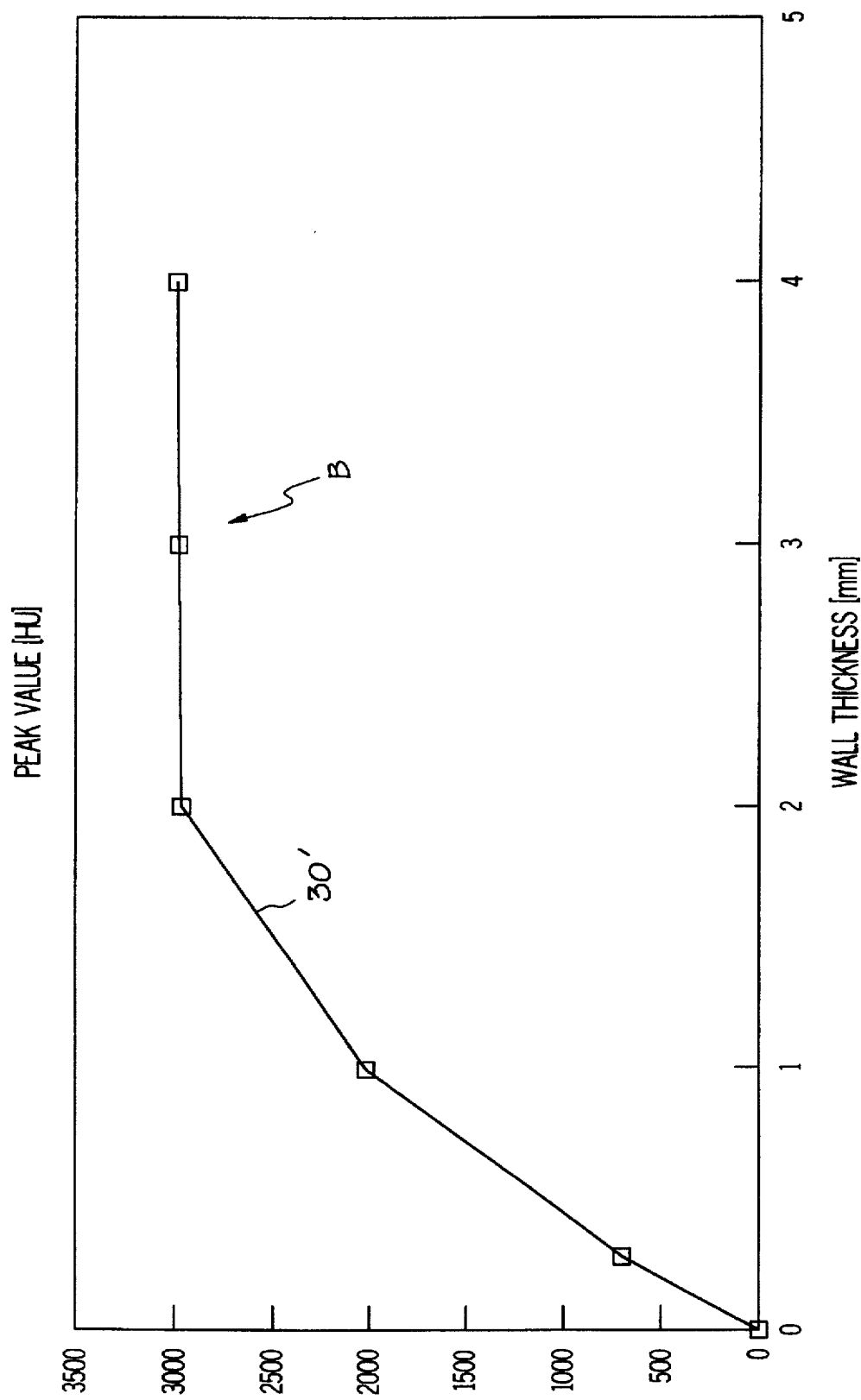
FIG. 3 is a graphical illustration of a calibration curve according to the present invention.

After obtaining scans of the phantom 8 at each cortical width, the resulting images are subjected to an algorithm that identifies the exact center of the cortical insert. A circular region of interest, with the approximate size of the outer cortical boundary, is moved in small increments until the sum of all pixels within this region shows a maximum. The average pixel values within concentric shells provide a radial profile of the density distribution across the cortex. The radial profiles of each discrete cortical width of the phantom 8 are illustrated in FIG. 2. As long as the cortical structure is large enough, e.g., 3.0 mm and 4.0 mm, the correct cortical density is indicated by the peak values of each curve. Specifically, the 4.0 mm curve peak 20 and the 3.0 mm curve peak 22 indicate a substantially correct cortical density of the phantom. The remaining curve peaks 24, 26, 28 correspond to density values increasingly lower than the correct density value of the phantom 8. The representation of peak cortical density versus cortical width, illustrated in FIG. 3, shows that the minimum structural width necessary for accurate density evaluations is about 2.5 mm. Accordingly, the minimum resolution value of the particular scanner in use is about 2.5 mm.

As will be appreciated by one of ordinary skill in the art, the methodology of the present invention can be executed with a conventional CT scanner in communication with a computer including a digital controller programmed to perform the steps of the present invention or to cause such steps to be performed. The computer also preferably includes a display device in communication with the digital controller, wherein the digital controller is further programmed to cause display of one or several of the radial density profiles, the peak density value $D_1$, the structural width $w_1$, the first curve of density versus width, and the structural density value $D_2$, and a data input device in communication with the digital controller, wherein the digital controller is further programmed to receive a signal from the data input device indicative of the peak density value $D_1$.

Bone, particularly cortical bone or trabecular bone, is the major structure of interest with respect to this invention.

However, it is contemplated that any other structure or any tissue that shows with at least a minimal amount of contrast relative to its surrounding tissue can be analyzed this way.

Although the present invention is discussed in the context of structural widths which most commonly correspond to cortical bone (0.2 mm to 3.0 mm), it is contemplated by the present invention that, if the resolution of the particular CT scanner in use permits, the apparatus and method of the present invention can be employed to measure and analyze trabecular bone which commonly has width dimensions in the area of about 10 μm to 100 μm.

Having described the invention in detail and by reference to preferred embodiments thereof, it will be apparent that modifications and variations are possible without departing from the scope of the invention defined in the appended claims.

COMPUTER PROGRAM LISTING

Subroutine Get_width ( Dens, N, Loc_out, Loot Loc_in)

Implicit None

| | | |
|---|---|---|
| Integer*4 | Dens(80) | Density profile |
| Integer*4 | N | Number of values in profile |
| Real*4 | Loc_out | Exterior threshold crossing |
| Integer*4 | Loc | Location of maximum density |
| Real*4 | Loc_in | Interior threshold crossing |
| Real*4 | Hi_dens | Peak density value |
| Real*4 | Thresh_in | Interior threshold |
| Real*4 | Thresh_out | Exterior threshold |
| Integer*2 | Ii | Index |
| Integer*2 | Ij | Index |
| Integer*2 | Kk | Index |
| Real*4 | Thresh_rel /0.45/ | Relative threshold |
| Real*4 | St_dens /2330/ | Outer density |
| Real*4 | M_dens /1882/ | inner density |
| Real*4 | Peak_est /18200/ | Density of structure |

```
C Find maximum value in profile.
Hi_dens = -999.0
Do Ii = 1, N
    If (Dens(Ii) .GE. Hi_dens ) Then
        Hi_dens = Dens(Ii)
        Loc = Ii
    Endif
End do
C Find point where outer wall crosses threshold.
C Assume outer value to be St_dens.
Thresh_out = St_dens + (Peak_est - St_dens) * Thresh_rel
If (Hi_dens .LT. Thresh_out) Then
    Loc_out = Loc
Else
    Kk = 1
    Do While ((Dens(Kk) .LT. Thresh_out) .AND. (Kk .LE. Loc))
        Kk = Kk + 1
    End do
    If (Kk .GE. Loc) Then
        Loc_out = Loc
    ElseIf (Kk .EQ. 1) Then
        Loc_out = 1
    Else
        Kk = Kk - 1
        Loc_out = Kk + (Thresh_out - Dens(Kk)) /
                    (Dens(Kk + 1) - Dens(Kk))
    :
    Endif
Endif C Find point where inner wall crosses threshold.
C Assume inner value to be M_dens.
Thresh_in = M_dens + (Peak_est - M_dens) * Thresh_rel
If (Hi_dens .LT. Thresh_in) Then
    Loc_in = Loc
Else
```

COMPUTER PROGRAM LISTING
-continued

```
    Kk = Loc
    Do While ((Dens(Kk) .GE. Thresh_in) .AND. (KK .LT. N))
        Kk = Kk + 1
    End do
    If (Kk .GT. N) Then
        Loc_in = Loc
    Else
        Loc_in = Kk - (Thresh_in - Dens(Kk)) /
                    (Dens(Kk - 1) - Dens(Kk))
    :
    Endif
Endif
Return
End
```

I claim:

1. A method of measuring the density of a structure comprising the steps of:

obtaining X-ray image data of a structure with a computed tomography scanner;

establishing a radial density profile of said structure based upon the obtained X-ray image data;

identifying a peak density value $D_1$ along said density profile;

identifying a structural width $w_1$ of said structure;

interpolating a first curve of density versus width from a point defined by coordinates $w_1$ and $D_1$; and identifying a maximum density value of said first curve to establish a structural density value $D_2$.

2. A method of measuring the density of a structure as claimed in claim 1 wherein said step of interpolating said first curve comprises the steps of:

obtaining X-ray image data of a plurality of phantoms with said computed tomography scanner wherein each of said phantoms has a known density and a plurality of known widths;

plotting a series of curves, each of said curves representing peak density values of each phantom as a function of structural width, and each of said curves including a maximum peak density value; and interpolating said first curve based upon the paths of said series of curves.

3. A method of measuring the density of a structure as claimed in claim 1 wherein said structure is selected from the group consisting of cortical bone or trabecular bone.

4. A method of measuring the density of a structure as claimed in claim 1 wherein said first estimated structural width corresponds to the width of a cortex of a bone.

5. A method of measuring the density of a structure as claimed in claim 1 wherein said first estimated structural width corresponds to the width of an individual trabecula.

6. An apparatus for measuring the density of a structure comprising:

a computed tomography scanner; and a digital controller in communication with said computed tomography scanner, said digital controller being programmed to establish at least one radial density profile of said structure based upon X-ray image data obtained by said computed tomography scanner;

identify a peak density value $D_1$ along said density profile;

identify a structural width $w_1$ of said structure;

interpolate a first curve of density versus width from a point defined by coordinates $w_1$ and $D_1$; and identify a maximum density value of said first curve to establish a structural density value $D_2$.

7. An apparatus for measuring the density of a structure as claimed in claim 6 further comprising a data input device in communication with said digital controller, wherein said digital controller is further programmed to receive a signal from said data input device indicative of the peak density value $D_1$.

8. An apparatus for measuring the density of a structure as claimed in claim 6 further comprising a display device in communication with said digital controller wherein said digital controller is further programmed to cause display of said radial density profile, said peak density value $D_1$, said structural width $w_1$, said first curve of density versus width, said structural density value $D_2$, and combinations thereof.

9. An apparatus for measuring the density of a structure as claimed in claim 6 wherein said digital controller is further programmed to:

cause phantom X-ray image data of a plurality of phantoms to be stored and plotted as a series of curves, said phantom X-ray image data being indicative of a peak density value of each phantom as a function of phantom structural width, each of said phantoms having a known density and a plurality of known widths; and interpolate said first curve based upon the paths of said series of curves.

10. An apparatus for measuring the density of a structure as claimed in claim 6 wherein said structure is selected from the group consisting of cortical bone or trabecular bone.

11. An apparatus for measuring the density of a structure as claimed in claim 6 wherein said first estimated structural width corresponds to the width of a cortex of a bone.

12. An apparatus for measuring the density of a structure as claimed in claim 6 wherein said first estimated structural width corresponds to the width of an individual trabecula.

13. A method of measuring the width of a structure comprising the steps of:

obtaining X-ray image data of a structure with a computed tomography scanner;

establishing a radial density profile of said structure from the obtained X-ray image data;

calculating a first threshold value and a second threshold value;

identifying a first radial position corresponding to a point on said radial density profile where said radial density profile rises above said first threshold value;

identifying a second radial position corresponding to a point on said radial profile where said radial density profile falls below said second threshold value;

measuring a difference between said first radial position and said second radial position; and determining the width of the structure as a function of said measured difference.

14. A method of measuring the width of a structure as claimed in claim 13 wherein said first threshold value is calculated by multiplying a first density difference by an optimized percentage threshold, and wherein said second threshold value is calculated by multiplying a second density difference by said optimized percentage threshold.

15. A method of measuring the width of a structure as claimed in claim 13 wherein said first density difference is a difference between a density of the structure and a density of a first adjacent material, and said second density difference is a difference between the density of the structure and a density of a second adjacent material.

16. A method of measuring the width of a structure as claimed in claim 15 wherein said first density value is the sum of said first threshold value and the density of said first adjacent material, and wherein said second density value is the sum of said second threshold value and the density of said second adjacent material.

* * * * *